United States Patent [19]

Kirsch et al.

[11] 4,166,703

[45] Sep. 4, 1979

[54] TESTING OF FIBROUS COALESCER ELEMENTS

[75] Inventors: Milton Kirsch, Canoga Park; Robert W. Melvold, Simi Valley, both of Calif.

[73] Assignee: Rockwell International Corporation, El Segundo, Calif.

[21] Appl. No.: 851,029

[22] Filed: Nov. 14, 1977

[51] Int. Cl.² ............................................. G01N 21/06
[52] U.S. Cl. ................................. 356/442; 210/23 R; 290/573; 356/70
[58] Field of Search .................. 356/208, 70, 103, 201, 356/209, 301; 210/23 R

[56] References Cited

U.S. PATENT DOCUMENTS

| | | | |
|---|---|---|---|
| 3,736,790 | 6/1973 | Pontello | 356/237 X |
| 3,851,976 | 12/1974 | Meier | 356/208 X |
| 4,003,661 | 1/1977 | Yamano | 356/201 |

Primary Examiner—John K. Corbin
Assistant Examiner—Bruce Arnold
Attorney, Agent, or Firm—L. Lee Humphries; Henry Kolin; Clark E. DeLarvin

[57] ABSTRACT

A method of testing fibrous elements for their ability to effectively coalesce and separate water from an impure petroleum compound selected from the group consisting of crude oil and distillate fractions thereof. The method comprises introducing a reproducible emulsion consisting essentially of water and a substantially pure organic solvent into contact with a fibrous, coalescer element contained in a test zone. Separate streams of coalesced water and organic solvent are withdrawn from the zone. The predominant stream is passed between a source of light and a light-measuring means. The intensity of the light received by the light-measuring means is indicative of, and used as, the criterion for determining the acceptability of the coalescer element.

5 Claims, 1 Drawing Figure

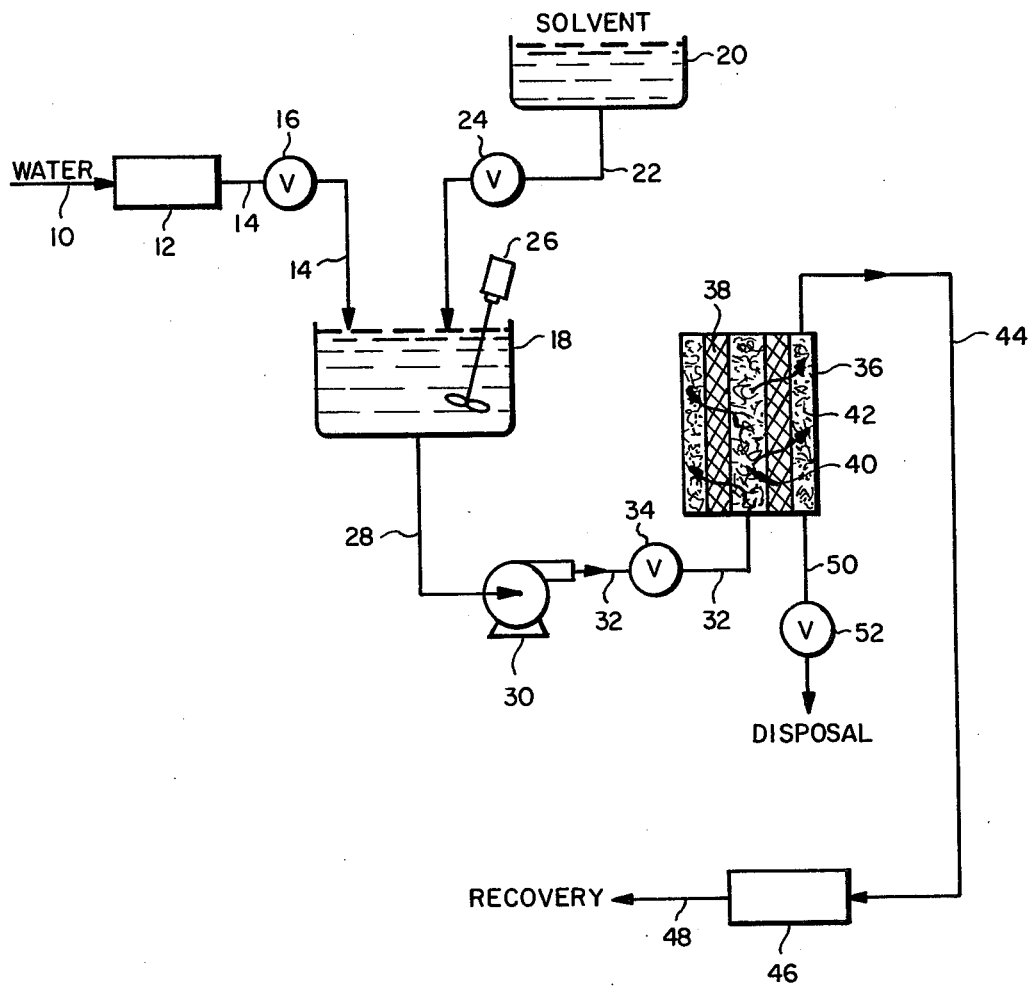

TESTING OF FIBROUS COALESCER ELEMENTS

BACKGROUND OF THE INVENTION

1. Field of the Invention

This invention relates to the removing of dispersed contaminants from fluids. It more particularly relates to a method of testing fibrous coalescer elements for their ability to remove emulsified water initially present from hydrocarbon fuels, lubricating oils and other similar organic fluids, which in addition to water may contain other impurities such as water soluble surfactants and inorganic solids. It also relates to a method of testing fibrous coalescer elements for their ability to coalesce oil from oily water.

2. Description of the Prior Art

It is frequently necessary to remove liquid contaminants such as water or solutions of salt from fuels or other petroleum distillates if they are to be suitable for their intended use. For example, emulsified water droplets in aircraft fuels may freeze forming ice crystals which could plug fuel lines, interrupting the flow of fuel to the engine. Further, gross quantities of water carried in the fuel stream may cause engine failure or malfunction, and indeed could cause loss of the aircraft. When the entrained water contains dissolved salts, corrosion of fuel system components may also result. In addition, water or aqueous solutions of salt in hydraulic fluids or other types of petroleum products, including lubricating oils could cause similar problems along with corrosion of the system components. Removal of oil from oily waste water such as bilge water or ballast water on shipboard is required before discharge of the waste water into the waterway or coastal water is legally permissible. Techniques for cleaning up oily waste water prior to discharge have been developed. Various means have been employed heretofore to remove such liquid contaminants; however, a particular problem exists when one attempts to remove water from an emulsion of the same and fuel oils, lubricating oils and the like.

In accordance with one prior technique, the contaminated fluid or fuel is passed through an electric field which is employed as a means of causing coalescence of dispersed aqueous contaminants thereby facilitating their removal from the fluid stream by gravity separation or other mechanical means.

A disadvantage of the electric type of coalescer is that the electrodes must be relatively widely spaced to avoid shorting where other than small amounts of water are present in the oil. In addition, they require a source of electrical energy for their operation, and when the fluid is flammable there always exists the hazard of an explosion in the event of an electrical short. Further, such devices have a relatively high initial cost and require a skilled operator for their maintenance and operation.

Another method of removing such aqueous impurities from oil or oily impurities from water are mechanical filters sometimes described as filter/separators or alternatively, fibrous coalescer elements. These devices have the advantage of not requiring electrical power for their operation or skilled operators. However, they do suffer from one disadvantage. Specifically, if the surface of the elements are contacted or contaminated with a surface active material, their effectiveness of coalescing are substantially reduced or possible totally eliminated. During the manufacture of the elements and their assembly, it is not uncommon for some of the elements to become contaminated with surface active agents to such a degree that they are unacceptable for their intended purpose. Hundreds of thousands of such fibrous coalescer elements are bought annually by the various Department of Defense agencies. These elements are supposed to conform to certain military specifications, for example MIL-F-52308, in their ability to coalesce free water from petroleum fuels, or to MIL-S-52846 in their ability to coalesce oil from oily waste water. In practice, however, it has been reported that individual lots of such elements are often found not to perform as expected. Indeed, it has been reported by certain authorities that in practice defective elements sometimes constitute as much as 30% of the accepted manufacturer's lots. This is believed to result from the types of screening presently available. Specifically, the various lots of coalescer elements are subjected to random sampling, with individual selected elements being utilized to filter and coalesce water from contaminated fuels. The effluent is then chemically analyzed for water and particulate component concentration to determine the effectiveness of that particular element. However, since the fuels also frequently contain surfactants as impurities, the elements become contaminated during testing and are seldom useable thereafter for their commercially intended purpose.

It also will be appreciated that in random sampling, the probability of the sample reflecting the true acceptability of the total lot will depend upon the size of sample taken; i.e., the larger the sample size, the larger the probability that it is truly representative of the lot. However, it conversely follows that the larger the sample size, the fewer elements remain for use for their intended purpose. Clearly, therefore, there exists a need for an improved method of testing such fibrous coalescer elements, to determine their acceptability for use either in removing or separating water from various petroleum products.

SUMMARY OF THE INVENTION

In accordance with the present invention, there is provided a method of testing fibrous coalescer elements for their ability to effectively coalesce and separate water from various petroleum compounds such as crude oil and distillate fractions thereof, including among other things, gasoline, kerosene, jet fuel, diesel fuel, fuel oil, lubricating oil, and the like. It is a particular advantage of the present invention that the individual elements tested may then be used for their intended purpose with a high degree of confidence that they will perform satisfactorily. Thus, the method of the present invention may be used either for testing a random selection of fibrous coalescer elements or for 100% screening of entire production lots.

In accordance with the present method, a reproducible emulsion of known composition consisting essentially of water and an organic solvent, substantially free of any impurities, is introduced into contact with the fibrous element being tested which is contained in a test zone. Separate streams of coalesced water and the organic solvent are withdrawn from the zone. One of the separate streams is passed between a source of light and a light-measuring means. The intensity of light received by the light-measuring means is measured, and the intensity measurement utilized to determine the acceptability of the fibrous elements.

It has been found that the method of the present invention provides an economically viable way of distinguishing between acceptable and unacceptable fibrous coalescer elements. Further, it is readily capable of indicating degrees of acceptability or effectiveness in coalescing water from emulsions of the same and crude oils or their distillate products.

BRIEF DESCRIPTION OF THE DRAWING

The sole FIGURE is a schematic representative of an apparatus for practicing the method of the present invention.

DETAILED DESCRIPTION OF THE INVENTION

The present invention utilizes an emulsion of known composition consisting essentially of water and an organic solvent. The water can be distilled and of high purity; however, it is not essential to the practice of the invention. Ordinary tap water has been found to be satisfactory provided it has been filtered to remove most of the suspended solids. Specifically, the water should contain less than about 50 ppm of suspended solids when it is the major component.

The organic solvent utilized may be either a hydrocarbon solvent or a halogenated hydrocarbon solvent. The particular solvent selected is not critical, provided it meets certain criteria. First, the solvent must have a density which is at least about 10% greater or less than that of water. Preferably the organic solvent will have a specific gravity of from about 1.2 to 1.5 or 0.6 to 0.9. If the density of the solvent is too similar to that of water, the time required for gravity separation becomes impractical for a commercial method of testing coalescer elements.

The selected solvent also should be substantially free of any entrained or suspended solids when it is the major component. Generally it is preferred that the selected solvent contain less than about 1 ppm of solid particulate. It is an essential feature of the invention that the emulsion be substantially free of any surface active agents. Obviously, this requires that the water or organic solvent, whichever is the major component, also be substantially free of any surface active agents. By substantially free, it is meant that the emulsion should contain less than about 5 ppm and preferably less than about 0.1 ppm surface active agents. Surface active agents are, of course, agents which, when in solution, cause surfaces to be more readily wetted. Because of this property solutions of surface active agents frequently are also referred to as wetting agents, penetrants, dispersing agents, emulsifying agents and the like. For a more comprehensive discussion of the compounds which exhibit this characteristic, reference may be had to the Encyclopedia of Chemical Technology, Kirk-Othmer, Volume 13.

Advantageously, the selected solvent will have a low boiling point to facilitate rapid evaporation of the solvent from the fibrous coalescer elements once they have been tested. The solvent also must have, of course, a normal boiling point above 0° C. to permit the formation of the desired water and solvent emulsion at atmospheric pressure. Therefore, the preferred organic solvents will have a boiling point within the range of from about 5° to 90° C. and preferably within the range of 20° to 70° C. A low viscosity also is desirable to allow rapid drainage of the organic solvent from the tested coalescer elements. Thus, the preferred organic solvent will have a viscosity within the range of from about 0.2 to 0.7 centipoise. Certain of the fluorinated organic solvents are particularly desirable in spite of their higher cost since they are less flammable or even nonflammable. A representative list of suitable organic solvents include, among other, N-Pentane, iso-Pentane, neo-Pentane, various commercially available kerosenes, and the various fluorinated organic solvents sold by duPont under their tradenames Freon MF, Freon 21, Freon 114, and Freon 113. Chlorinated hydrocarbons such as chloroform and carbon tetrachloride also are suitable dense solvents.

The organic solvent and water are mixed and subjected to shearing forces to form an emulsion in which one of the constituents is present in a minor amount and the other in a major amount. Generally, the minor constituent will comprise from about 0.01 to 0.5 wt.% of the emulsion and preferably from about 0.05 to 0.2 wt. %. It will be appreciated that the present invention is applicable to testing fibrous coalescer elements which are intended to separate minor amounts of water from an oil, or elements which are intended to separate minor amounts of oil from a stream consisting predominantly of water. For convenience, the invention will be described with respect to elements for removing trace amounts of water from hydrocarbon streams.

The emulsion of known composition is passed through the fibrous coalescer elements to be tested to separate the emulsion (assuming the coalescer element is functioning properly) into its separate constituent parts, namely water and solvent. The major constituent then is introduced into some means for measuring its turbidity, the preferred means being a source of light and a light intensity-measuring means. Any remaining amount of the minor constituent from the initial emulsion will affect the turbidity or clarity of the major constituent. This change affects the intensity of the light measured, and thus is directly correlatable to the effectiveness or acceptability of the coalescer element.

The specific device utilized to measure turbidity is not critical and numerous such devices are known to those versed in the art. Examples of various models commercially available are: Monitek Turbidimeter Model 215/130, made by Monitor Technology; Totamitor, made by Keene Corporation, Fluid Handling Division.

Referring now to the drawing, water from a source not shown is passed through conduit 10 and through filter 12 to remove any entrained solids. Filtered water leaves filter 12 via conduit 14 and flow regulating valve 16 for introduction into mixing tank 18. An organic solvent is withdrawn from holding tank 20 and passed through conduit 22 and flow regulating valve 24 for introduction into mixing tank 18. In mixing tank 18, the mixture of organic solvent is subjected to high shearing forces, for example, by motor driven mixing blade 26, to form an emulsion of organic solvent and water having a known or fixed predetermined composition.

The emulsion is withdrawn from mixing tank 18 via conduit 28 for introduction into pump 30. The emulsion leaves pump 30 via conduit 32 and flow control valve 34 for introduction into a test zone defined by housing 36. Contained within housing 36 is a fibrous coalescer element 38 to be tested. The emulsion is introduced into housing 36 where it flows generally through the interior section 40 defined by element 38 and outwardly through fibrous coalescer element 38 which causes the water within the emulsion to coalesce and form large droplets which collect in an outer zone 42 defined by housing 36 and fibrous coalescer element 38. In zone 42 the water and organic solvent separate by gravity. From an upper portion of housing 36 a stream of substantially pure solvent (assuming the organic solvent has a density less than that of water and the fibrous coalescer element is a satisfactory one) is withdrawn via conduit 44 for introduction into a turbidity measuring means 46. Generally, the turbidity measuring means will comprise a source of light and a light-measuring means. The light intensity-measuring means may measure the amount of light directly passing through the organic solvent. Alternatively, the light intensity-measuring means may measure the intensity of indirect light which is scattered as a result of the turbidity of the organic solvent. In either instance the intensity of the light measured is directly correlatable with the effectiveness of the particular filter element being tested.

The solvent leaving turbidity measuring means 46 is withdrawn via a conduit 48 for recovery and preferably recyled for testing additional coalescer elements. The water contained within housing 42 is periodically drained off via a conduit 50 and drain valve 52.

EXAMPLE 1

The following example is set forth to demonstrate the utility of the method of the present invention in testing fibrous coalescer elements. Four commercially available fiber elements were tested utilizing substantially pure kerosene as the solvent. Emulsions containing varying amounts of water were prepared and introduced into the filter elements utilizing an arrangement of apparatus substantially as depicted in the drawing. The turbidity of the effluent organic stream was measured using a commercially available apparatus. Samples of the effluent also were analyzed for their water content. The results of these tests are set forth in the table below:

TABLE I

| Filter Element Bendix # | Influent Water Content ppm | Turbidity | Total Effluent Water Content ppm | Effluent Free (Undissolved) Water Content ppm |
|---|---|---|---|---|
| 3 | 10,000 | 4,300 | 558 | 466 |
| 3 | 1,000 | 900 | 143 | 51 |
| 4 | 1,000 | 430 | 91 | 0 |
| 3 | 2,000 | 2,740 | 227 | 135 |

From the foregoing results, it is readily seen that the turbidity measurement is directly correlatable to the performance of the individual coalescer elements. Thus, the present invention provides a convenient, non-destructive method of testing fibrous coalescer elements and assessing their relative performance or acceptability.

EXAMPLE 2

The following series of tests were performed to demonstrate the method of the present invention as applied to fibrous coalescer elements for the removal of minor amounts of oil emulsified in water. Several commercial fibrous coalescer elements from two different manufacturers were obtained and tested in substantially the same manner as set forth in Example 1, except in this instance water was the major component. Specifically, the emulsion comprised 200 ppm of an organic solvent (a commercially available kerosene substantially free of surfac-tants) in water. The turbidity of the effluent water was measured and the water was also analyzed for oil content. The results of the tests are set forth in Table II below:

TABLE II

| Element No. | Turbidity of Effluent Water | Solvent Content of Effluent Water ppm |
|---|---|---|
| 1 | 5.0 | 0 |
| 2 | 5.0 | 0 |
| 3 | 5.5 | 1 |
| 4 | 5.5 | 1 |
| 5 | 5.5 | 1 |
| 6 | 5.5 | 1 |
| 7 | 16.0 | 5 |
| 8 | 7.5 | 2 |
| 9 | 5.5 | 1 |
| 10 | 5.5 | 1 |
| 11 | 16.5 | 5 |

Any element that permits no more than 15 ppm organic solvent to remain in the effluent water complies with the manufacturer's specifications. Thus, it is seen from the table that all the elements were "good"; however, the present method is capable of distinguishing between those "good" elements which coalesce better than others. Indeed, the present method is so sensitive to quality that a "bad" element (one which permitted more than 15 ppm of organic solvent to remain in the effluent water) would produce a turbidity reading of about 50. Thus, this example again demonstrates the utility of the present invention as a convenient non-destructive method of testing and evaluating fibrous coalescer elements.

It will, of course, be realized that various modifications can be made in the design and operation of the present invention without departing from the spirit thereof. Thus, while the principal, preferred construction, and mode of operation of the invention have been explained and what is now considered to represent its best embodiment has been illustrated and described, it should be understood that within the scope of the attendant claim the invention may be practiced otherwise than as specifically illustrated and described.

What is claimed is:

1. A method of testing fibrous elements for their ability to effectively coalesce and separate into separate components an emulsion of water and petroleum compounds selected from the group consisting of crude oil and distillate fractions thereof comprising the steps of:
   introducing a reproducible emulsion consisting essentially of water and an organic solvent substantially free of surface active agents into contact with a fibrous element contained in a test zone, one of said water or organic solvent being present as a major component of said emulsion,
   withdrawing separate streams of coalesced water and organic solvent from said zone,
   passing one of said separate streams comprising the major component between a source of light and a light-measuring means,
   measuring the intensity of light received by said light-measuring means while said stream is passing between said source of light and said light-measuring means, and
   determining the acceptability of said fibrous element based on the intensity of the light so measured.

2. The method of claim 1 wherein the emulsion consists essentially of from about 0.01 to about 0.5 wt.% water and the balance is an organic solvent having a boiling point within the range of from about 5° to 90° C., a viscosity within the range of from about 0.2 to 0.7 centipoise and a density which is at least about 10% greater or less than that of water.

3. The method of claim 2 wherein the emulsion contains less than about 5 ppm of surface active agents.

4. The method of claim 1 wherein the emulsion consists essentially of from about 0.01 to about 0.5 wt.% of said organic solvent and the balance is water containing less than about 50 ppm of suspended solids.

5. The method of claim 4 wherein the emulsion contains less than about 5 ppm of surface active agents.

* * * * *